United States Patent [19]
Wolf

[11] Patent Number: 5,368,023
[45] Date of Patent: Nov. 29, 1994

[54] REUSABLE TRACHEOSTOMY COLLARS

[76] Inventor: Gloriann C. Wolf, 1300 McDowell Rd. Apt. 104, Naperville, Ill. 60563

[21] Appl. No.: 42,499

[22] Filed: Apr. 2, 1993

[51] Int. Cl.⁵ ............................................. A61M 16/00
[52] U.S. Cl. ....................... 128/207.17; 128/DIG. 26; 604/179
[58] Field of Search .................... 128/207.14, 207.17, 128/200.24, DIG. 26; 604/174, 179

[56] References Cited

U.S. PATENT DOCUMENTS

| | | | |
|---|---|---|---|
| 4,331,144 | 5/1982 | Wapner | 128/207.17 |
| 4,592,351 | 6/1986 | Smith | 128/207.17 |
| 4,676,233 | 6/1987 | Scheinburg | 602/18 |
| 4,774,943 | 10/1988 | Yu | 128/207.14 |
| 4,844,061 | 7/1989 | Carroll | 128/207.17 |
| 4,958,631 | 9/1990 | Sarkozi | 602/18 |
| 5,005,564 | 4/1991 | Grundei et al. | 602/18 |
| 5,027,801 | 7/1991 | Grim | 602/16 |
| 5,029,577 | 7/1991 | Sarkozi | 602/18 |
| 5,042,477 | 8/1991 | Lewis | 128/207.17 |
| 5,056,508 | 10/1991 | Brunell | 602/18 |
| 5,060,661 | 10/1991 | Howard | 128/845 |

FOREIGN PATENT DOCUMENTS 2259863 12/1972 Germany.

Primary Examiner—Edgar S. Burr
Assistant Examiner—Eric P. Raciti
Attorney, Agent, or Firm—Greer, Burns & Crain, Ltd.

[57] ABSTRACT

A soft reusable tracheostomy collar is provided for holding a tracheostomy tube securely in place. The collar is specifically made with machine washable materials. The present tracheostomy collar provides increased comfort and stability to the tracheostomy tube, alleviating leaks and dislodged tracheostomy tubes. In addition, the present tracheostomy collar includes two tying tapes of equal lengths with easily threadable plastic tips to place through the tracheostomy tube flanges and tie at the back of the neck. The present collar also is available with two additional tying tapes to tie across the front to hold a mechanical breathing device in place. The present tracheostomy collar is provided in a variety of different sizes to accommodate all possibilities. Furthermore, the relatively simple design makes the present collar easy and inexpensive to manufacture.

9 Claims, 2 Drawing Sheets

REUSABLE TRACHEOSTOMY COLLARS

BACKGROUND-FIELD OF INVENTION

This invention relates to a neck collar, specifically for holding a tracheostomy tube securely in place.

BACKGROUND-DESCRIPTION OF PRIOR ART

Supply companies and hospitals commonly distribute twill tape and gauze sponges for holding a tracheostomy tube in place. However, users object to this method since it is both cumbersome and expensive to use. The twill tape needs to be cut to be removed with tracheostomy tube changes or when the gauze sponges become soiled and require changing. The twill tape is then damaged thereby rendering it impossible to reuse. The gauze sponges do not stand up well to moisture and also need to be replaced frequently by the user, thereby rendering this method both bothersome and an added expense to contend with.

Thereafter, inventors created foam pads to be used in place of the gauze sponges. However, these foam pads are cumbersome and unsightly. They require much more manipulation to apply and remove, causing discomfort to the user. They also need to be replaced after each use, rendering them expensive for the user. Finally, the user may be allergic to the foam pads, causing inflammation and skin breakdown.

One type of tracheostomy holder that has been proposed is U.S. Pat. No. 4,331,144. This holder breaks down easily if laundered and can only be used a couple of times. The material and VELCRO brand hook and loop fastener tapes tend to crumble and fail after repeated laundering. Finally, the VELCRO fastener tapes tend to rub the skin at times, causing irritation and discomfort.

The disadvantages of the tracheostomy holder disclosed in U.S. Pat. No. 4,331,144 are:

(a) Its manufacture is of materials that are fragile and breaks down easily if laundered, rendering it expensive for the user.
(b) Its application procedure are clumsy and difficult, causing discomfort for the user.
(c) It may cause inflammation and skin breakdown due to the VELCRO fastener tapes which rub the skin, and allergic reactions caused by the materials used.
(d) It can only be used one time, making it expensive to the user.
(e) Its design is neither cost effective nor beneficial to the environment.
(f) It is unpreposing to the user's attire.
(g) It provides no means of holding a mechanical breathing device securely to the tracheostomy tube.

OBJECTS AND ADVANTAGES

My own tracheostomy collar utilizes a material that is soft, comfortable and capable of repeated washings without damaging the collar. This collar is of a simple construction and is very cost effective for the user. Several objects and advantages of this present tracheostomy collar are:

(a) To provide a collar that has easily threadable ties with plastic tips, making it less cumbersome and easier to apply.
(b) To provide a collar that has strings of equal lengths to tie across the front to hold a mechanical breathing device securely in place.
(c) To provide a collar of 100% cotton blend material to protect the skin and is comfortable for the user.
(d) To provide a collar with increased stability, thus alleviating leaks and dislodged tracheostomy tubes.
(e) To provide a collar that is in a variety of different sizes to well accommodate all possibilities.
(f) To provide a collar that is available in an assortment of colors to enable the user to accessorize.
(g) To provide a collar that may be personalized for the user, thus adding to the user's attire and making it attractive.
(h) To provide a collar that is cost effective for the user.
(i) To provide a collar that is made of materials that stand up well to repeated launderings and uses.

Further objects and advantages are to provide a collar which can be used easily and reused without damage to the collar, which is simple to use and inexpensive to manufacture. Still further objects and advantages will become apparent from a consideration of the ensuing description and drawings.

DRAWING FIGURES

In the drawings, closely related figures have the same number but different alphabetic suffixes.

DESCRIPTION OF THE PREFERRED EMBODIMENTS

Figure 1A:
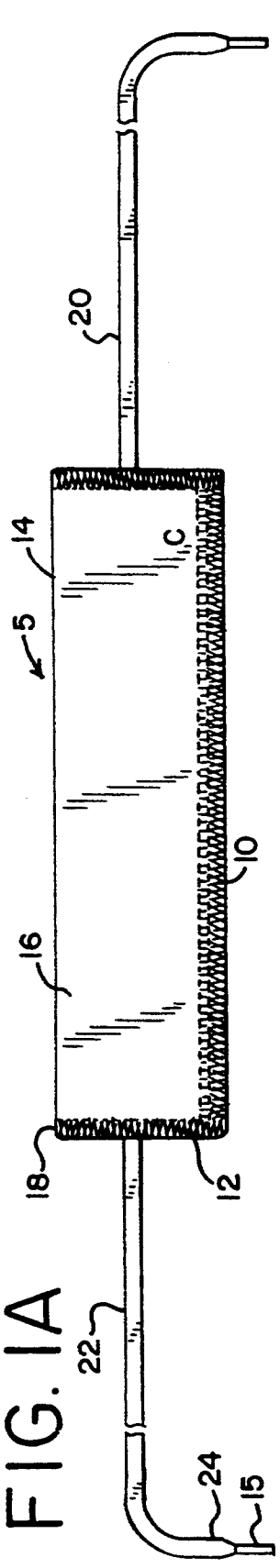
FIGS. 1A and 1B are front elevational views of the present tracheostomy collar, depicting the construction and string placement of the two and four string tracheostomy collar embodiments, respectively.

The body of this tracheostomy collar, generally designated 5, is best seen in FIG. 1A. An alternate embodiment is shown in FIG. 1B and is generally designated 7, wherein it is indicated at 10 a ¼" baseline stitching, a ¼" stitching at the ends 12 and a soft rolled edge along the top 14.

Figure 1B:
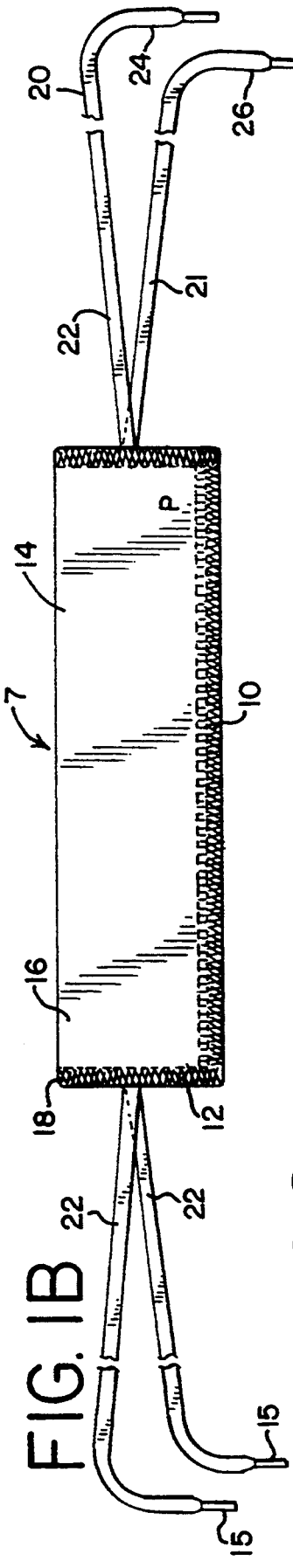

The collar embodiments depicted in FIGS. 1A and 1B vary in size about 1–4" in diameter 16 and have different lengths depending on the user's neck size.

Figure 7:
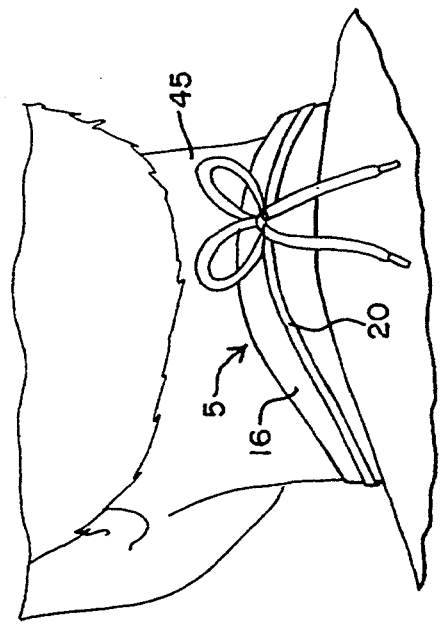
FIG. 7 shows a frontal view of the tracheostomy collar in place about the neck of the user shown with an attached mechanical breathing device.

Attached to the ends 18 of the collar 5 are cotton tying tapes 20 and 21 (best seen in FIG. 1B) of convenient equal lengths, of approximately ten inches or so. The tapes 20 and 21 which may also be referred to as ties or strings, each have a connecting end 22 adjacent the body 5. Also, each tape 20 is provided with a flange end 24 opposite the connecting end 22. The tape 21, also referred to as a device tape, has a device end 26 opposite the corresponding connecting end 22. Each of the tapes 20, 21 are provided with plastic tips 15 connected at the flange end 24 of tape 20 and the device end 26 of tape 21. One tying tape 20 is for stabilizing the tracheostomy tube as shown in FIG. 4, and the additional tying tape 21 may be used for attaching a mechanical breathing device 50 as seen in FIG. 7.

Figure 2:
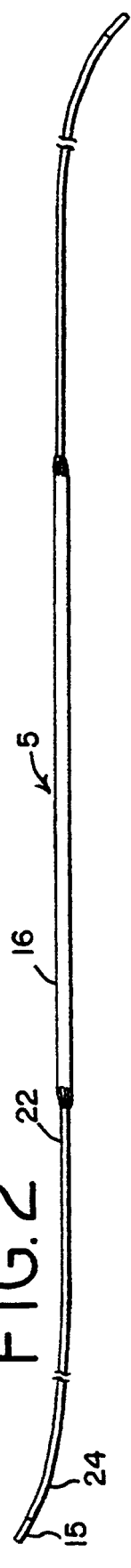
FIG. 2 is an overhead plan view of the collar of FIG. 1A depicting the thickness of the tracheostomy collar.
Figure 3:
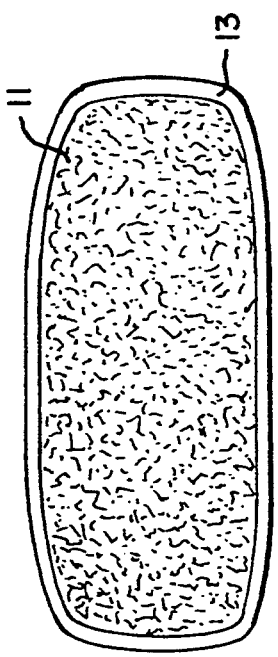
FIG. 3 is a diagrammatic vertical sectional of the interior construction if the tracheostomy collar.

The completed collar is very narrow having a thickness of approximately ⅜" as shown in FIG. 2. Referring now to FIG. 3, the interior 11 of the collar contains a soft fill such as 100% cotton. The covering and exterior materials 13 are preferably a 100% cotton velour blend material. The materials used are machine and hand washable. If desired, the body 5 may be colored and/or personalized to suit the user.

Figure 4:
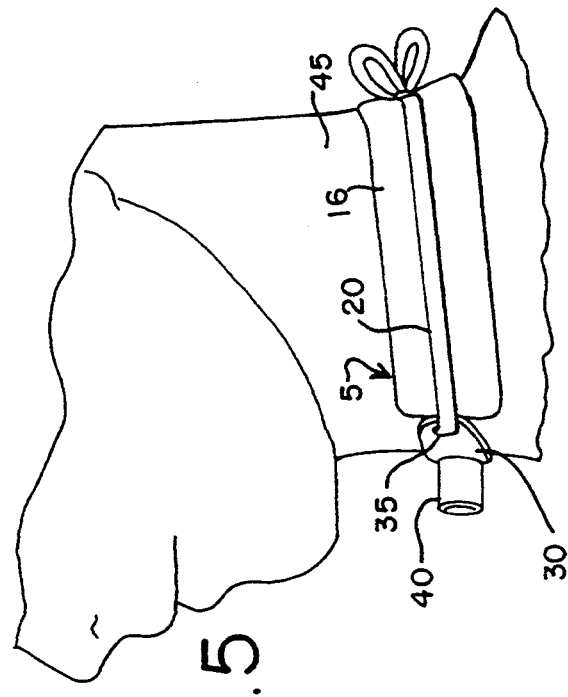
FIG. 4 is a frontal view of the tracheostomy collar in place about the neck of a user.
Figure 5:
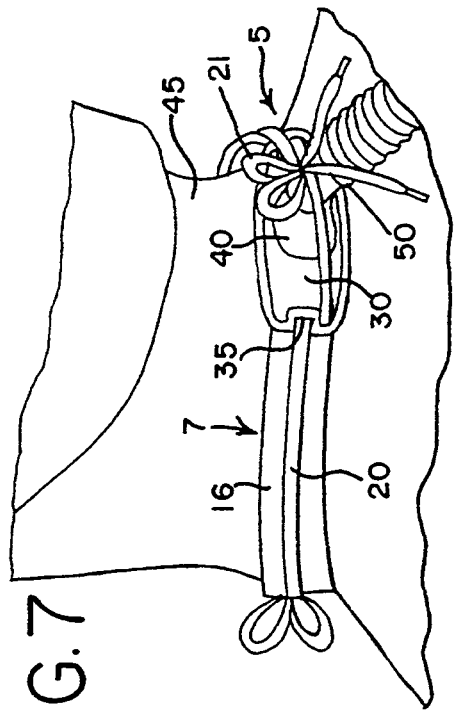
FIG. 5 is a side view of the tracheostomy collar in place about the neck of the user.
Figure 6:
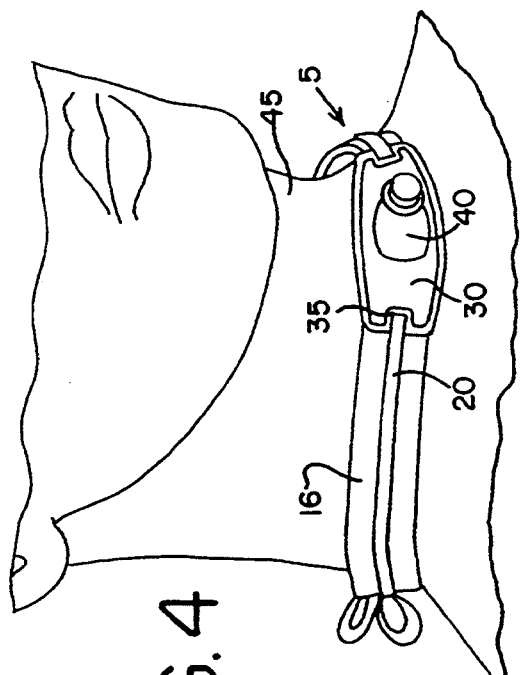
FIG. 6 is a rear view of the tracheostomy collar in place about the neck of the user.

In operation, referring to FIGS. 4-6, the flange end 24 of one of the cotton, plastic tipped 15 tying tapes 20 is threaded right or left through the aperture 35 in the flange 30 of the appropriate side on the tracheostomy tube 40. The collar is positioned to meet the flange 30 as seen in FIG. 4 so the tying tape is not touching the skin along the neck. The body of the collar 5 is looped around the neck 45 as in FIG. 5 and the flange end 24 of the opposite tying tape is threaded through the aperture 35 in the flange 30 of the tracheostomy tube 40. The opposite side of the collar is positioned to meet the flange 30 as in FIG. 4 so that the tying tapes are no longer touching the skin. The tying tapes 20 are then looped back across the collar as seen in FIG. 5 and tied securely in the back of the neck 45 as seen in FIG. 6.

SUMMARY

This tracheostomy collar provides an improved material and methods for its use which avoids many of the shortcomings of the previously available tracheostomy holders.

In accordance with the present methods and tracheostomy holder a thin soft material with a layer of soft fabric is provided to fit about a users neck. The soft fill material is 100% cotton with a soft 100% cotton velour blend outer layer.

Lightweight, soft and strong materials are used. There are no sharp edges or corners to be encountered. To the ends of the tracheostomy collar are added cotton tying tapes with easily threadable plastic tips. Thus the collar is placed where needed about the users neck, the ends brought around to the flanges of the tracheostomy tube and the tying tapes are used to firmly tie the collar in the position needed. It is desirable to provide a soft reusable and economical tracheostomy collar which has a simple construction and is inexpensive to manufacture.

Thus the scope of this tracheostomy collar should be determined by the appended claims and their legal equivalents rather than by the examples given.

I claim:

1. A tracheostomy collar for securely stabilizing a tracheostomy tube on a patient's neck to provide protection from undue discomfort, the tracheostomy tube having at least one flange with a corresponding aperture to which the collar is securable, the collar comprising:

a main body having a first end and a second end;

a first tying tape having a connecting end operably connected to said first end of said main body, and a flange end opposite said connecting end, said flange end being insertable through a corresponding one of the apertures in the at least one flange for operably connecting said first end of said main body to the tracheostomy tube, with said first end of said main body adjacent to the flange so that in use said main body is interposed between said first tying tape and a patient's neck; and a second tying tape having a connecting end operably connected to said second end of said main body, and a flange end opposite said connecting end of said second tape, said flange end of said second tape being insertable through a corresponding one of the apertures in the at least one flange for operably connecting said second end of said main body to the tracheostomy tube, with said second end of said main body adjacent to the flange, so that said main body is interposed between said second tying tape and the patient's neck with said main body drawn around the patient's neck, said first and second tying tapes, after being brought across said main body, being securable to one another for holding the tracheostomy tube in place.

2. A tracheostomy collar as defined in claim 1 wherein said flange ends of said first and second tying tapes contain a tip operably connected thereto.

3. A tracheostomy collar as defined in claim 1 wherein said main body has a laterally flattened tubular construction and includes an interior material and an exterior material surrounding said interior material.

4. A tracheostomy collar as defined in claim 3 wherein said exterior material is folded over said interior material and stitched closed creating, on said main body, a folded edge and a stitched edge.

5. A tracheostomy collar for securely stabilizing a tracheostomy tube and an independent breathing device on a patient's neck to provide protection from undue discomfort, the tracheostomy tube having a pair of flanges, each with a corresponding aperture to which the collar is securable, the collar comprising:

a main body having a first end and a second end;

a first set of two tying tapes including a first flange tape and a second flange tape, said first and second flange tapes each having a connecting end operably connected respectively to said first and second ends of said main body, and a flange end opposite said connecting end, said flange ends being insertable through the corresponding aperture in one of the flanges for operably connecting said first and second ends of said main body to the tracheostomy tube, with said first and second ends of said main body adjacent to the corresponding flanges so that in use said main body is interposed between said first and second flange tapes and the patient's neck with said main body drawn around the patient's neck, said first and second flange tapes, after being brought across said main body, being securable to one another for holding the tracheostomy tube in place;

a second set of two tying tapes including a first device tape and a second device tape, said first and second device tapes each having a connecting end operably connected respectively to said first and second ends of said main body, and a device end opposite said connecting end, said first and second device tapes being securable to one another for holding the independent breathing device in place on a patient's neck.

6. A tracheostomy collar as defined in claim 5 wherein said flange ends of said first and second tying tapes each contain a tip operably connected thereto.

7. A tracheostomy collar as defined in claim 5 wherein said device ends of said first and second tying tapes each contain a tip operably connected thereto.

8. A tracheostomy collar as defined in claim 5 wherein said main body has a laterally flattened tubular construction and includes an interior material and an exterior material surrounding said interior material.

9. A tracheostomy collar as defined in claim 8 wherein said exterior material is folded over said interior material and stitched closed creating, on said main body, a folded edge and a stitched edge.

* * * * *